United States Patent
Vresilovic et al.

(10) Patent No.: US 7,850,730 B2
(45) Date of Patent: Dec. 14, 2010

(54) METHOD AND APPARATUS FOR IMPLANTING A HYDROGEL PROSTHESIS FOR A NUCLEUS PULPOSUS

(75) Inventors: Edward Vresilovic, Ardmore, PA (US); Michael Keane, Dowingtown, PA (US); Thomas Peter Schaer, Landenberg, PA (US); Amy Arthur, Philadelphia, PA (US); Wamis Singhatat, Malvern, PA (US)

(73) Assignee: Synthes USA, LLC, West Chester, PA (US)

( * ) Notice: Subject to any disclaimer, the term of this patent is extended or adjusted under 35 U.S.C. 154(b) by 14 days.

(21) Appl. No.: 11/391,245

(22) Filed: Mar. 29, 2006

(65) Prior Publication Data

US 2006/0276802 A1  Dec. 7, 2006

Related U.S. Application Data

(60) Provisional application No. 60/665,836, filed on Mar. 29, 2005.

(51) Int. Cl.
*A61F 2/44* (2006.01)
(52) U.S. Cl. .................. 623/17.11; 623/17.12; 606/99; 606/86 R
(58) Field of Classification Search .............. 606/102, 606/90, 92–94, 105, 279, 86 R, 96, 97, 99, 606/86 A; 623/17.11–17.16, 16.11, 1.11, 623/1.23
See application file for complete search history.

(56) References Cited

U.S. PATENT DOCUMENTS 4,896,669 A * 1/1990 Bhate et al. .................. 606/194

(Continued)

FOREIGN PATENT DOCUMENTS

WO  WO 01/87195 A1  11/2001

(Continued)

OTHER PUBLICATIONS

International Searching Authority, "Communication Relating to the Results of the Partial International Search", from counterpart International application No. PCT/US2006/011454.

*Primary Examiner*—Todd E Manahan
*Assistant Examiner*—Tara R Carter
(74) *Attorney, Agent, or Firm*—Stroock & Stroock & Lavan, LLP

(57) ABSTRACT

An instrument for inserting an elongated hydrogel prosthesis into an intervertebral disc includes an insertion cannula that is inserted through the annulus fibrosus of an intervertebral disc to provide access to the nucleus region of the disc, an elongated hydrogel prosthesis packaged within a tubular container adapted to be coupled to a proximal end of the insertion cannula, and a source of fluid pressure adapted to be coupled to a proximal end of the tubular container. Auxiliary instruments for use in convenient insertion of the insertion cannula through the nucleus pulposus and providing for a complete and controlled passage of the hydrogel prosthesis through the insertion cannula are provided in a kit with the insertion cannula. A sizing apparatus for determining the volume of prosthesis to be inserted includes a catheter or cannula capable of being inserted through the insertion cannula into the nucleus region of the intervertebral disc and having at its distal end a balloon capable of being inflated within the intervertebral disc with a measurable volume of a fluid in order to determine the amount of hydrogel prosthesis to be injected.

18 Claims, 13 Drawing Sheets

U.S. PATENT DOCUMENTS

| | | | | |
|---|---|---|---|---|
| 5,171,280 | A * | 12/1992 | Baumgartner | 623/17.12 |
| 5,320,611 | A * | 6/1994 | Bonutti et al. | 604/264 |
| 5,716,416 | A * | 2/1998 | Lin | 623/17.16 |
| 5,800,549 | A * | 9/1998 | Bao et al. | 606/99 |
| 5,888,220 | A * | 3/1999 | Felt et al. | 128/898 |
| 6,248,131 | B1 * | 6/2001 | Felt et al. | 623/17.12 |
| 6,280,475 | B1 * | 8/2001 | Bao et al. | 623/17.16 |
| 6,306,177 | B1 * | 10/2001 | Felt et al. | 623/23.6 |
| 6,893,466 | B2 * | 5/2005 | Trieu | 623/17.16 |
| 7,077,865 | B2 * | 7/2006 | Bao et al. | 623/17.12 |
| 2002/0091387 | A1 * | 7/2002 | Hoogland | 606/61 |
| 2002/0156530 | A1 * | 10/2002 | Lambrecht et al. | 623/17.16 |
| 2003/0047126 | A1 * | 3/2003 | Tomaschko | 116/201 |
| 2004/0186471 | A1 * | 9/2004 | Trieu | 606/61 |
| 2005/0209602 | A1 * | 9/2005 | Bowman et al. | 606/90 |
| 2005/0216087 | A1 * | 9/2005 | Zucherman et al. | 623/17.16 |
| 2006/0009851 | A1 * | 1/2006 | Collins et al. | 623/17.16 |

FOREIGN PATENT DOCUMENTS

| | | |
|---|---|---|
| WO | WO 03/037166 A2 | 5/2003 |
| WO | WO 2004/100841 A1 | 11/2004 |

* cited by examiner

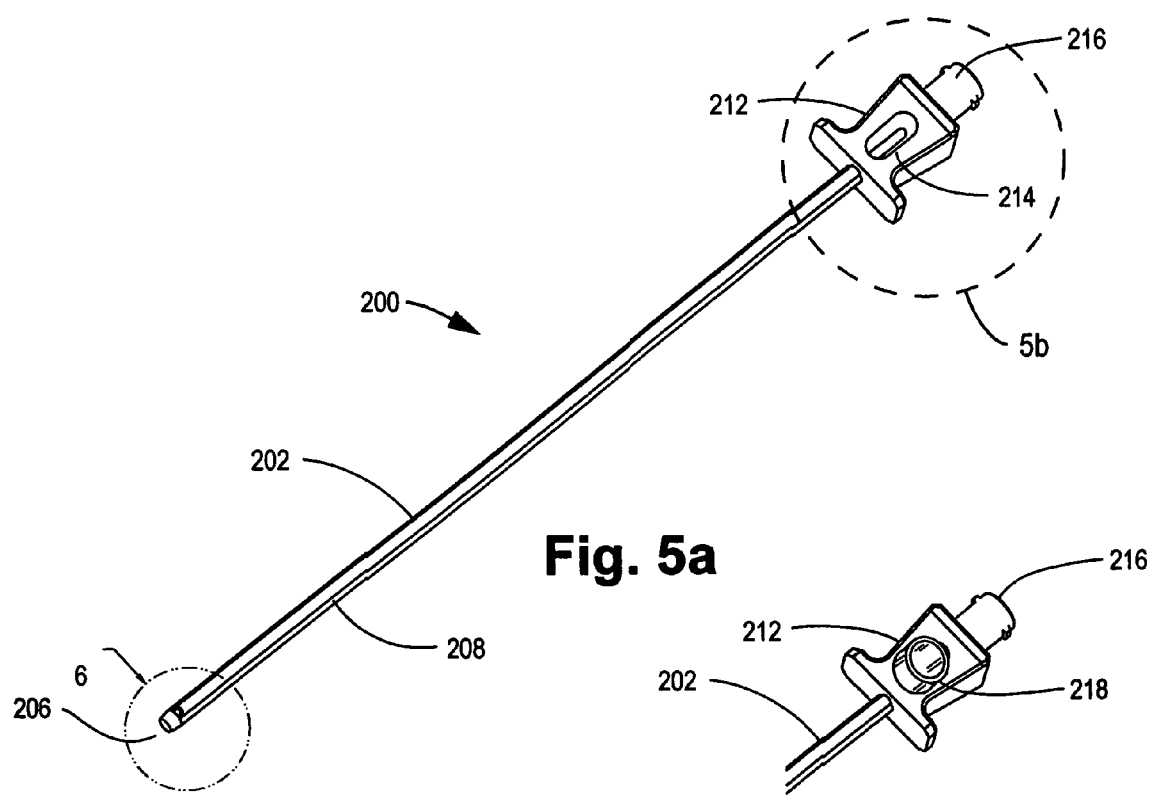
Fig. 5a
Fig. 5b
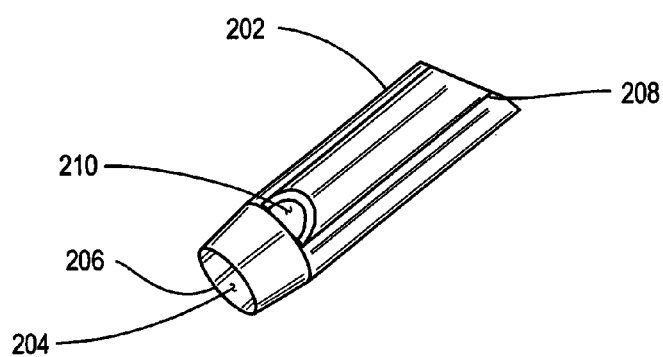
Fig. 6

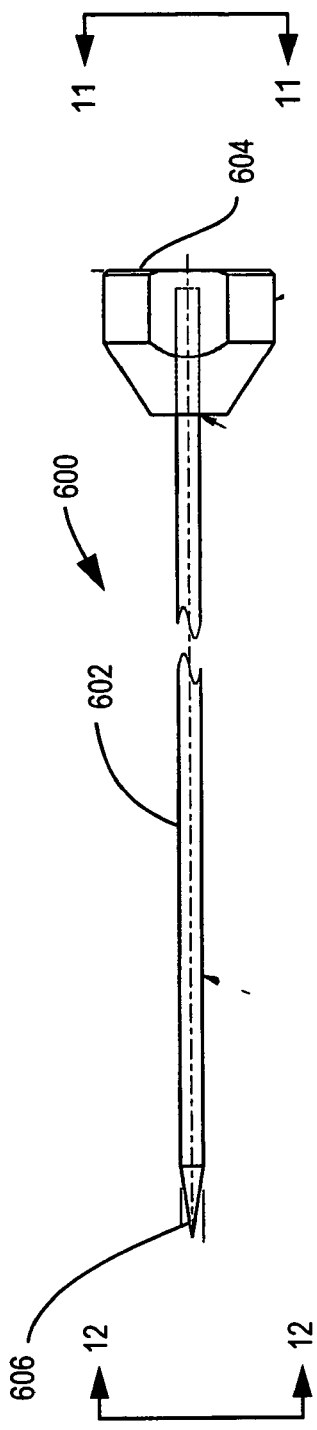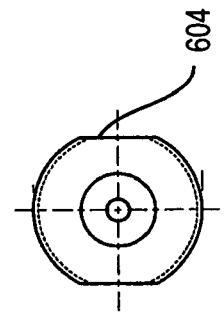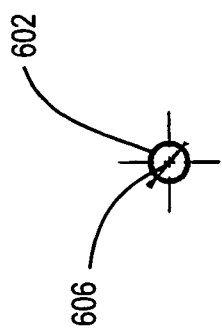
Fig. 10
Fig. 11
Fig. 12

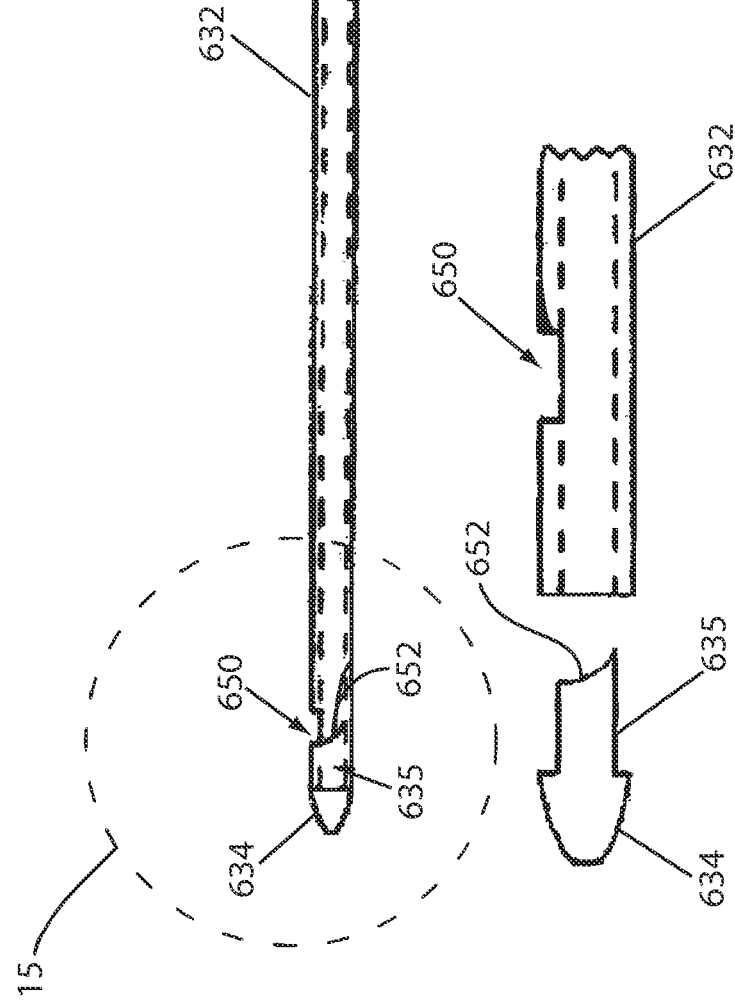

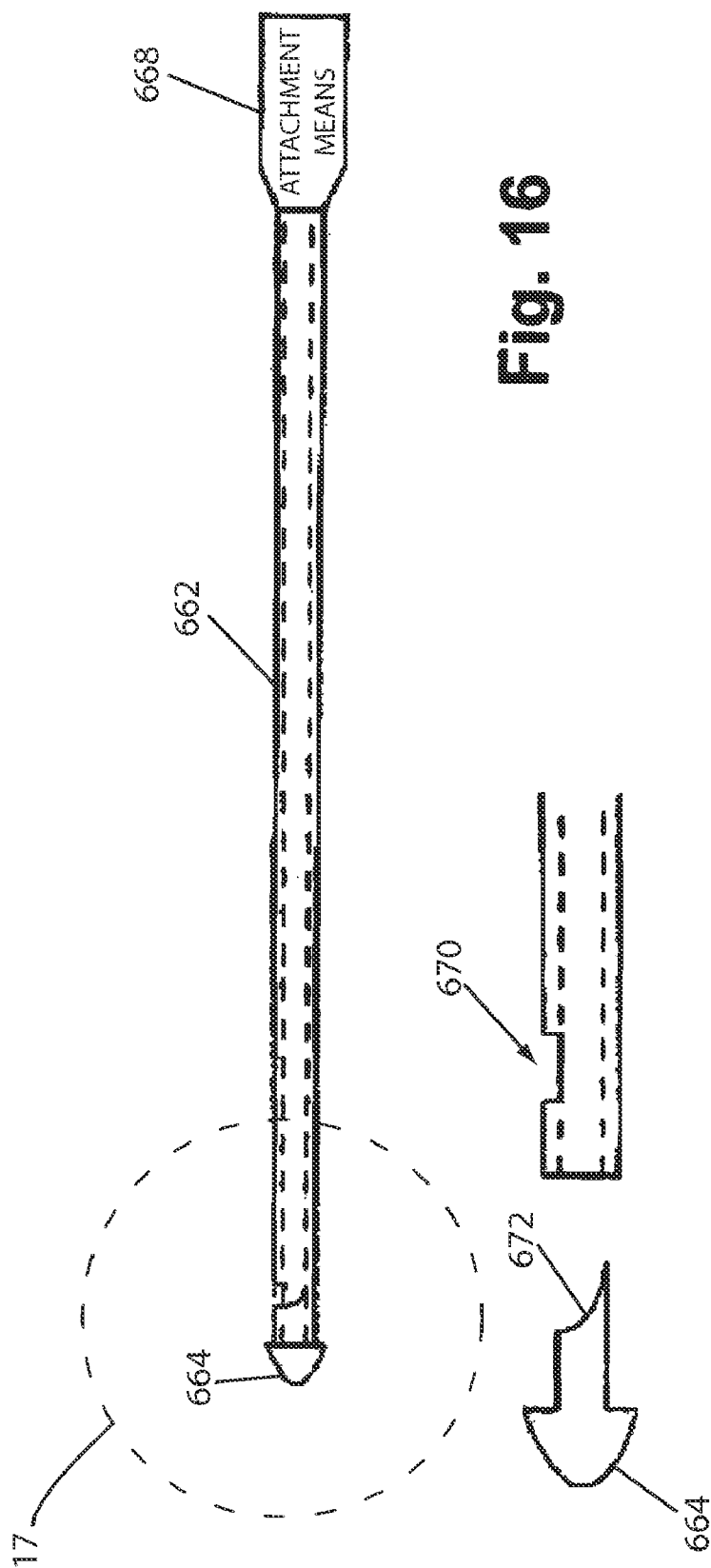

METHOD AND APPARATUS FOR IMPLANTING A HYDROGEL PROSTHESIS FOR A NUCLEUS PULPOSUS

CROSS-REFERENCE TO RELATED APPLICATIONS

This application claims the benefit of U.S. Provisional Patent Application No. 60/665,836, filed Mar. 29, 2005, the entire disclosure of which is incorporated herein by reference.

BACKGROUND OF THE INVENTION

1. Field of the Invention

This invention relates to prostheses for replacing or augmenting a nucleus pulposus of an intervertebral disk, and more particularly to apparatus for injecting a low modulus spinal implant into an intervertebral disc through a small portal.

2. Brief Description of the Prior Art

Chronic back pain, typically lower back pain, caused by injury or age-related degeneration of an intervertebral disc is a condition experienced by many patients.

Current treatment options for back pain range from conservative bed rest to highly invasive surgical procedures including spinal fusion and total disc replacement.

The human intervertebral disc is comprised of two major structures, an outer or peripheral tendinous structure, referred to as the annulus fibrosus or annulus, and an inner gelatinous nucleus pulposus located in a generally central region within the annulus fibrosus. Degeneration of the nucleus leads to disc degradation and loss of function. Consequently, another surgical option for the relief of back pain is replacement of the nucleus, leaving the annulus intact. The aim of nucleus replacement is to relieve pain, to restore healthy physiological function to the disc, and to prevent additional wear and degeneration of the annulus.

In view of the gelatinous nature of the nucleus pulposus, the use of hydrogels to replace the natural nucleus pulposus has been proposed, and materials and methods for such replacement have been proposed.

Hydrogels are typically formed from solid, generally insoluble hydrophilic polymers and, in their hydrated state, have a generally water-swollen structure. It has been proposed to design hydrogel implants that may have mechanical properties which approximate those of the natural nucleus pulposus, and to implant such hydrogel prostheses into the central region of an intervertebral disc, i.e., into the cavity normally occupied by the nucleus pulposus. Accordingly, a need has continued to exist for a method of determining the proper amount of a hydrogel prosthesis to be implanted in order to restore to the extent possible the natural mechanical properties and behavior of the intervertebral disc and for inserting such a hydrogel prosthesis.

SUMMARY OF THE INVENTION

This invention is a further development of the invention disclosed and claimed in U.S. patent application Ser. No. 11/134,309, filed May 23, 2005, the entire disclosure of which is incorporated herein by reference.

According to the invention a nucleus pulposus of an intervertebral disc can be supplemented or replaced by injecting a hydrogel into the nucleus pulposus region of an intervertebral disk. An instrument according to the invention for insertion of an elongated hydrogel prosthesis comprises an insertion cannula that is inserted through the annulus fibrosus of an intervertebral disc to provide access to the nucleus region of the disc, an elongated hydrogel prosthesis packaged within a tubular container adapted to be coupled to a proximal end of the insertion cannula, and a source of fluid pressure adapted to be coupled to a proximal end of the tubular container. Auxiliary instruments for use in convenient insertion of the insertion cannula through the nucleus pulposus and providing for a complete and controlled passage of the hydrogel prosthesis through the insertion cannula are provided in a kit with the insertion cannula. The invention also comprises a sizing balloon and associated cannula capable of being inserted through the insertion cannula into the nucleus region of the intervertebral disc and being inflated therein with a measurable volume of a fluid in order to determine the amount of hydrogel prosthesis to be injected into the nucleus pulposus region of the intervertebral disc. The amount of such hydrogel prosthesis to be implanted is that required to restore, to the extent possible, the natural mechanical properties of the intervertebral disc. This restoration may be accomplished by implanting a hydrogel prosthesis to fill any cavity naturally existing or surgically created within the intervertebral disc or to supplement the natural tissue of the intervertebral disc, thereby repressurizing the nucleus pulpous region and annulus fibrosus of the intervertebral disc. Although the method and apparatus of the invention are generally discussed herein below in terms of filling a cavity within a nucleus pulposus, it is to be understood that the invention is applicable for augmenting an intervertebral disc for all conditions needing such augmentation as recited above.

Accordingly, it is a feature of the invention to provide an instrument for insertion of an elongated hydrogel prosthesis into the nucleus pulposus region of an intervertebral disc. The said instrument enables the elongated hydrogel prosthesis to flow as if a fluid due to the lubricious and fluid boundary layers of the said hydrogel.

A further feature is to provide an instrument for measuring the volume of a defect or cavity in the nucleus pulposus region of an intervertebral disc in order to determine the volume of a prosthesis to be inserted therein.

Further features of the invention will be apparent from the description of the invention which follows and the associated drawings.

BRIEF DESCRIPTION OF THE DRAWINGS

FIG. 5a is a perspective view of the insertion cannula of FIG. 2. FIG. 5b shows a view of the handle of an alternate embodiment of the insertion cannula of FIGS. 2 and 5a, wherein the vent of the auxiliary channel is provided with a fluid coupling member.

FIG. 6 is a detail of the distal tip of the insertion cannula as indicated by the circle 6 in FIG. 5.

FIG. 10 is a side elevational view of the sharp guidewire instrument used with the insertion cannula of the invention.

FIG. 11 is an end elevational view of the handle end of the blunt guidewire of FIG. 10 taken in the direction indicated by 11-11 in FIG. 10.

FIG. 12 is an end elevational view of the pointed end of the blunt guidewire of FIG. 10 taken in the direction indicated by 12-12 in FIG. 10.

FIG. 14 is a side elevational view of an insertion cannula of the alternate embodiment of the invention of FIG. 13.

FIG. 15 is an exploded detail view of the tip region of the insertion cannula of FIG. 14.

FIG. 16 is a side elevational view of an another insertion cannula of the alternate embodiment of the invention of FIG. 13.

FIG. 17 is an exploded detail view of the tip region of the insertion cannula of FIG. 16.

DETAILED DESCRIPTION OF THE INVENTION

The invention includes a method and apparatus for injecting an elongated spinal implant into an intervertebral disc through a small portal. According to the invention, apparatus is provided for determining the volume of the cavity or defect to be filled by the prosthesis to be injected and for adjusting the injected volume to correspond with the measured volume.

The invention will be described with reference to the accompanying drawings.

Figure 1:
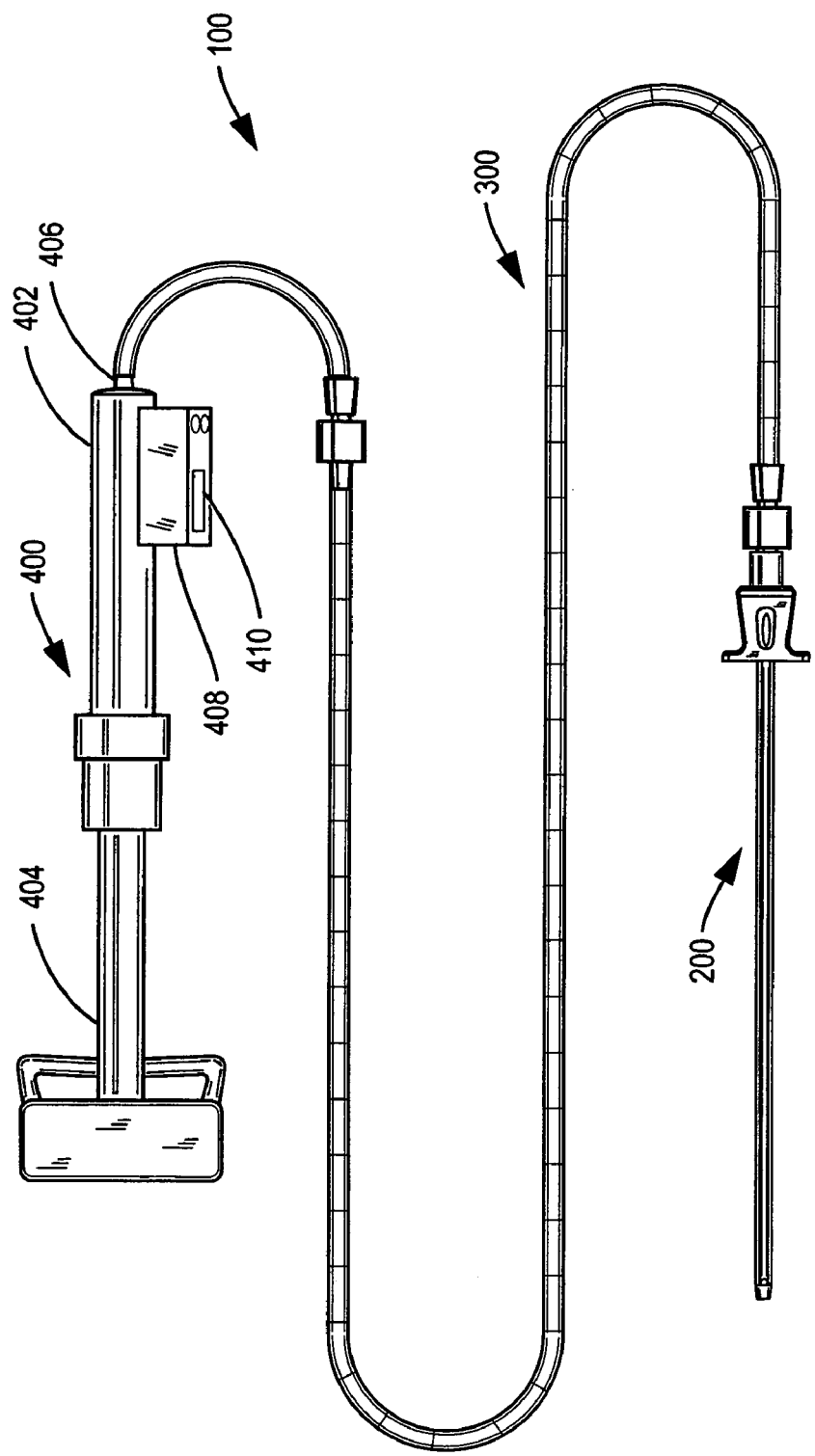
FIG. 1 shows a general view of an apparatus according to the invention, including an insertion cannula, a tubular package for an elongated hydrogel prosthesis, and a pressurizing syringe for applying fluid pressure to the prosthesis to inject it into an intervertebral disc.

FIG. 1 shows an embodiment of the hydrogel implantation apparatus 100 of the invention generally comprising an insertion cannula 200, a tubular container 300 for supplying an elongated hydrogel prosthesis, the tubular container 300 being generally sufficiently transparent to permit visualization of the prosthesis contained therein and bearing indicia 302 for determining a length of prosthesis to be injected as will be discussed in more detail below, and a pressurizing syringe 400.

The insertion cannula 200 is shown in more detail in FIGS. 2-6. In the description of the apparatus and components thereof the terms distal and proximal will be used with reference to the operator using the apparatus, e.g., a surgeon performing an implantation of a hydrogel prosthesis into the nucleus pulposus region of an intervertebral disc.

Figure 2:
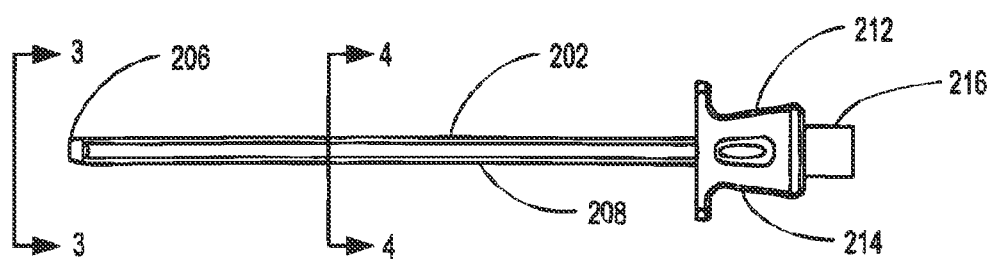
FIG. 2 is a plan view of an insertion cannula according to the invention.
Figure 3:
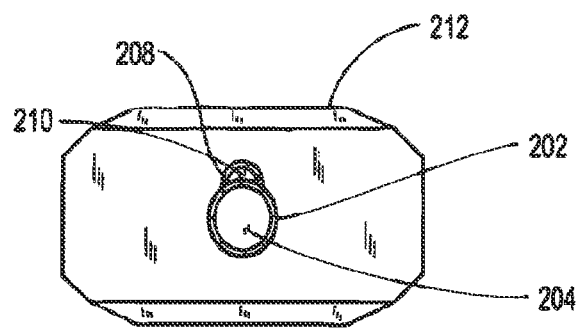
FIG. 3 is an end elevational view of the insertion cannula of FIG. 2 taken in the direction indicated as 3-3 in FIG. 2.
Figure 4:
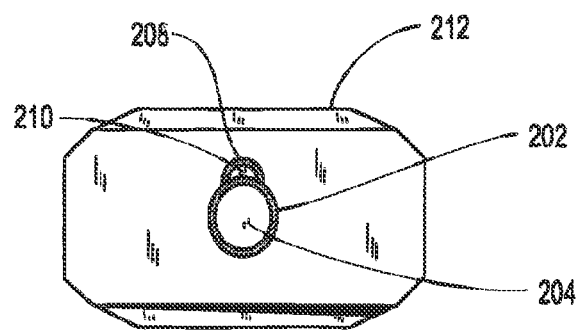
FIG. 4 is an elevational cross-sectional view of the insertion cannula of FIG. 2, taken as indicated by the line 4-4 in FIG. 2.
Figure 7:
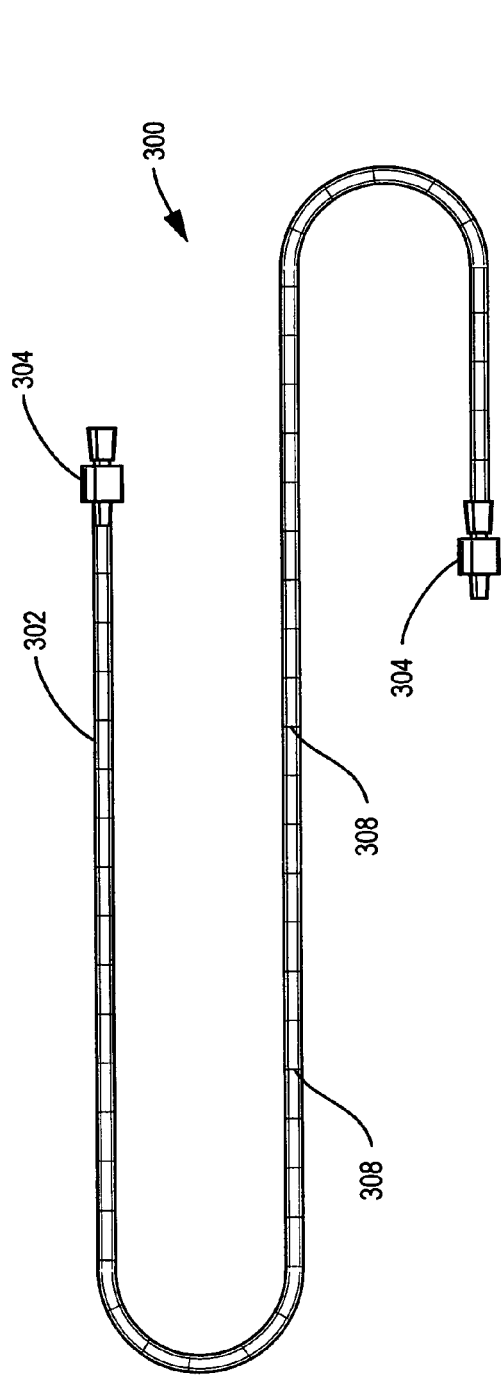
FIG. 7 is a general view of the tubular package for the elongated hydrogel prosthesis.

As shown in FIG. 2, the insertion cannula 200 includes a main delivery channel 202, having a lumen 204 with a tapered end 206, a secondary channel 208 provided along a side of the main delivery channel 202, having a lumen 210, and a handle 212 located at the proximal end of the insertion cannula 200. The handle 212 includes an opening 214 communicating with the auxiliary lumen 210 to provide a venting function. The opening 214 can also be provided with a coupling fitting (as shown in FIG. 5b) for connecting to other apparatus. The handle 212 also supports a fluid coupling 216, communicating with the delivery lumen 204, for connecting the delivery cannula to the storage tube 300 for the elongated hydrogel prosthesis.

The storage tube 300 for the hydrogel prosthesis comprises a generally transparent tube 302 provided with couplings 304 at either end for connecting to the delivery cannula 200 and to the pressurizing syringe 400 or other source of fluid pressure for forcing the prosthesis from the storage tube through the delivery cannula and into the intervertebral disc. The tube 302 is sufficiently transparent or translucent, or is provided with a transparent or translucent regions, e.g., a transparent or translucent stripe or a sites of transparent or translucent windows, (not specifically indicated) to permit the measurement of the selected amount of prosthesis and to monitor the prosthesis insertion process. The tube 302 is preferably provided with indicia 308 to facilitate determination of the length of prosthesis to be inserted, as will be discussed below.

The pressurizing syringe 400 is a generally conventional syringe of this type provided with a barrel 402, plunger 404 and coupling 406. Typically such syringes are equipped with a pressure transducer in an appropriate housing 408 with an indicator of the measured pressure 410.

The use of the apparatus 100, together with auxiliary instruments blunt guidewire 500 and sharp guidewire 600, will now be described.

Figure 8:
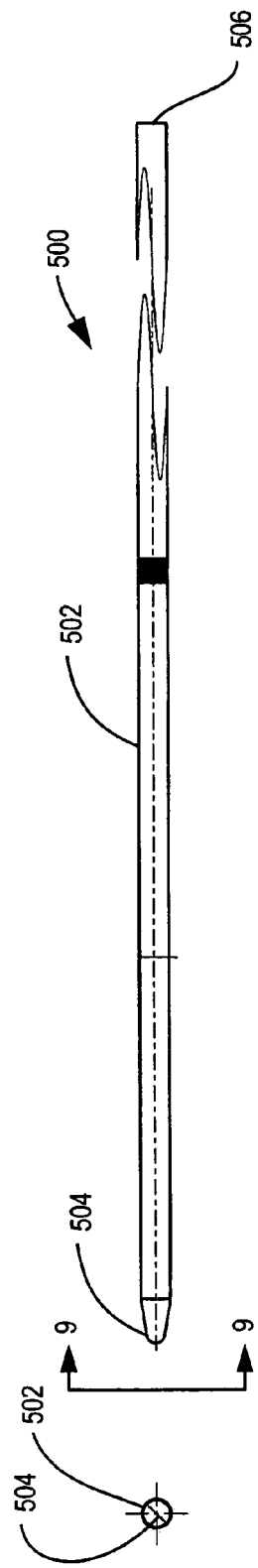
FIG. 8 is a side elevational view of the blunt guidewire instrument used with the insertion cannula of the invention.
Figure 9:
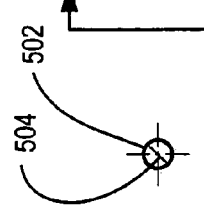
FIG. 9 is an end elevational view of the blunt guidewire of FIG. 8 taken in the direction indicated by 9-9 in FIG. 8.

After a suitable selection of a candidate patient for surgery, based on a conventional evaluation of symptoms and appropriate physical examination, the patient is prepared for surgery. Typically a posterior or postero-lateral approach is used. An access incision is made through the skin. In view of the relatively small dimensions of the prosthesis insertion instrument of the invention, the access incision can be relatively small. Thereupon, the blunt guidewire 500 (FIG. 8) is selected for the next step in the procedure. The blunt guidewire 500 has a shaft 502 sized for a sliding fit within the delivery lumen 204 of the delivery channel 202 of the delivery cannula 200. The shaft 502 has a tapered, but relatively blunt end 504, and a generally flat, or non-tapered end 506. The operation of the ends 504 and 506 of the blunt guidewire 500 will be explained in the following. After the access incision has been made, the blunt, tapered end 504 of the shaft 502 is carefully advanced through the tissue toward the intervertebral disc into which the prosthesis is to be inserted. The advance and positioning of the guidewire 500 is monitored by appropriate imaging, e.g., fluoroscopy, as the procedure is performed. The use of a guidewire 500 with a relatively blunt tip 504 at this stage of the procedure facilitates avoiding damage to delicate structures, including nerves, blood vessels, and the like, that are located in the general site of the surgery. When the tip 504 of the blunt guidewire 500 has reached the outer wall of the annulus fibrosus, the next step of the procedure is undertaken.

With the tip 504 of the blunt guidewire 500 resting against the outer wall of the annulus fibrosus, the delivery cannula 200 is fitted over the shank 502 of the guidewire 500 and carefully advanced through the tissue until its tapered tip 206 reaches the outer wall of the annulus fibrosus. Thereupon, the blunt guidewire 500 is removed and the next step of the procedure is initiated.

The sharp guidewire 600 (FIGS. 10-12) is then selected for the next step of the procedure. The sharp guidewire 600 has a shaft 602, with a handle 604 at the proximal end, and a sharp point 606 at the distal end. The shaft 602 has a diameter constructed for a sliding fit within the delivery lumen 204 of the delivery channel 202.

With the tip 206 of the delivery cannula 200 resting against the outer wall of the annulus fibrosus, the sharp guidewire is inserted into the delivery lumen 204 of the delivery channel 202 and advanced through the annulus fibrosus into the nucleus pulposus region of the intervertebral disk. Thereafter, the delivery cannula is advanced over the sharp guidewire until the distal end 206 thereof lies within the nucleus pulposus region of the intervertebral disc. This procedure is also performed with appropriate radiological or other monitoring means. Thereupon, the sharp guidewire 600 is removed, leaving an open channel from the exterior of the body into the nucleus pulposus region for further steps in the procedure.

Depending on the condition of the nucleus pulposus, the surgeon may proceed with any appropriate action to treat the nucleus pulposus or adjacent tissue. Thus, the surgeon may proceed directly with insertion of a prosthesis or with surgical preparation of a cavity to receive a prosthesis. Surgical tools adapted to excise tissue through a small opening are conventional, and any such tools, e.g., a cup biopsy forceps, may be used to excise tissue to prepare a suitable cavity. After a suitable cavity has been prepared, it is preferred to determine the size of the cavity available for implantation in order to preselect the correct amount of elongated hydrogel prosthesis. Methods of sizing a cavity within a body are known, and any such appropriate method may be used to determine the volume of the cavity to receive the prosthesis. It is preferred to insert a sizing balloon into the cavity and inflate the balloon with a suitable fluid, preferably a liquid, until the cavity is filled, as indicated by, e.g., increased resistance as indicated by relatively rapidly increasing pressure, internal pressure reaching a value predetermined to indicate satisfactory filling of the cavity, radiological monitoring using a radiopaque fluid, or the like. The volume of fluid required to fill the cavity is thus determined and recorded, and the balloon is deflated and withdrawn.

The surgeon then inserts through the insertion cannula a volume of hydrogel prosthesis generally equal to the volume of the cavity measured in the preceding step. Although the surgeon may proceed directly to inject the elongated hydrogel prosthesis, it is preferred to predetermine the amount of prosthesis to be injected by the following procedure. The storage tube 300 is coupled to the pressurizing syringe 400, or the like, in a sterile field. A storage tube is selected that has been preloaded with sufficient elongated prosthesis to provide an excess length of prosthesis within the storage tube 300 over that required to fill the prepared cavity. Thereupon, the pressurizing syringe is then operated to extrude the excess prosthesis, leaving in the storage tube 300 only the exact amount of prosthesis that is to be injected. Then the distal end of the storage tube 300 is coupled to the proximal end of the delivery cannula 200, and the pressurizing syringe 400 is operated to force the prosthesis out of the storage tube 300, through the delivery cannula 200, and into the cavity prepared in the nucleus pulposus region of the intervertebral disc. Although the entire length of the elongated prosthesis can be injected under fluid pressure, it is preferred to interrupt the injection when some, i.e., the final portion, of the prosthesis to be injected remains within the delivery cannula. Thereupon, the blunt guidewire is again selected, and the flat, or otherwise not intended for dissection, end 506, i.e., the end opposite the blunt dissection end 504, is inserted into the delivery lumen 204 of the delivery cannula 200 and advanced to extrude the final portion of the elongated hydrogel prosthesis into the cavity, and to assure that the terminal end of the prosthesis is positioned within the cavity away from the entrance aperture, thus minimizing the possibility of subsequent expulsion of the prosthesis through the implantation aperture.

Thereafter, the insertion cannula 200 and blunt guidewire 500 are withdrawn, and the surgical wounds are closed. Because the insertion aperture made in the annulus fibrosus by the procedure of the invention is relatively small, the surgeon may decide that any special closure procedure for that aperture is unnecessary. The remainder of the surgical closure procedure is conventional.

An alternate embodiment of the instrument for injecting an elongated prosthesis is illustrated in FIGS. 13-22.

Figure 13:
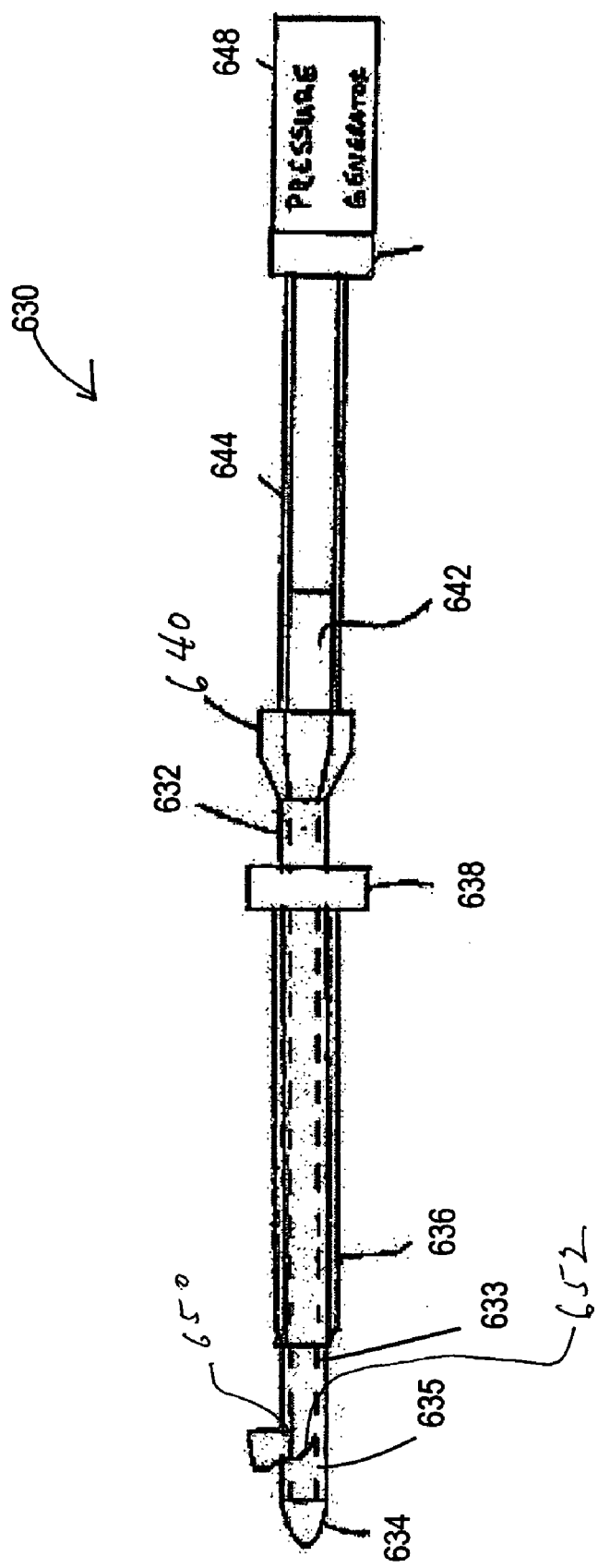
FIG. 13 is a schematic side elevational view of an alternate embodiment of the invention.
Figure 18:
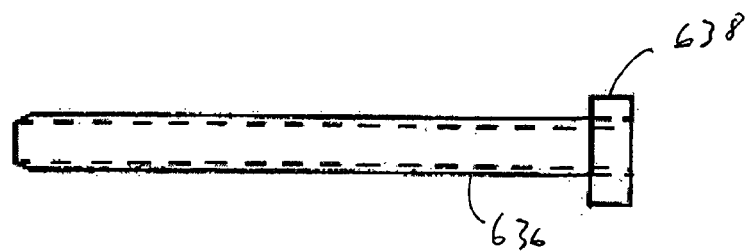
FIG. 18 is a side elevational view of the cutting sleeve used with the embodiment of FIG. 13.

FIG. 13 shows an apparatus 630 comprising a delivery cannula 632, a cutting sleeve (or outer cannula) 636 (illustrated in FIG. 18), which is slidably fitted over the delivery cannula 632 a storage tube 644, adapted to contain an elongated hydrogel prosthesis 642, and a pressure generator 648, which may be a pressurizing syringe such as used in the above-described embodiment of the invention.

The delivery cannula 632 has a delivery lumen 633 (shown in phantom) which is closed at its distal end by a plug tip 634 having a generally tapered tip for insertion through the annulus fibrosus of an intervertebral disc. The delivery cannula has a lateral-facing delivery aperture 650 located at its distal end, generally immediately proximal to the plug tip 634. The plug tip 634 is preferably provided with a shank 635 extending into the delivery lumen 633 and having a straight or curved ramp 652 to assist the delivery of the prosthesis through the lateral aperture 650. The proximal end of the delivery cannula 632 is provided with a coupling device 640 for coupling the proximal end to the storage tube 644.

Figure 19:
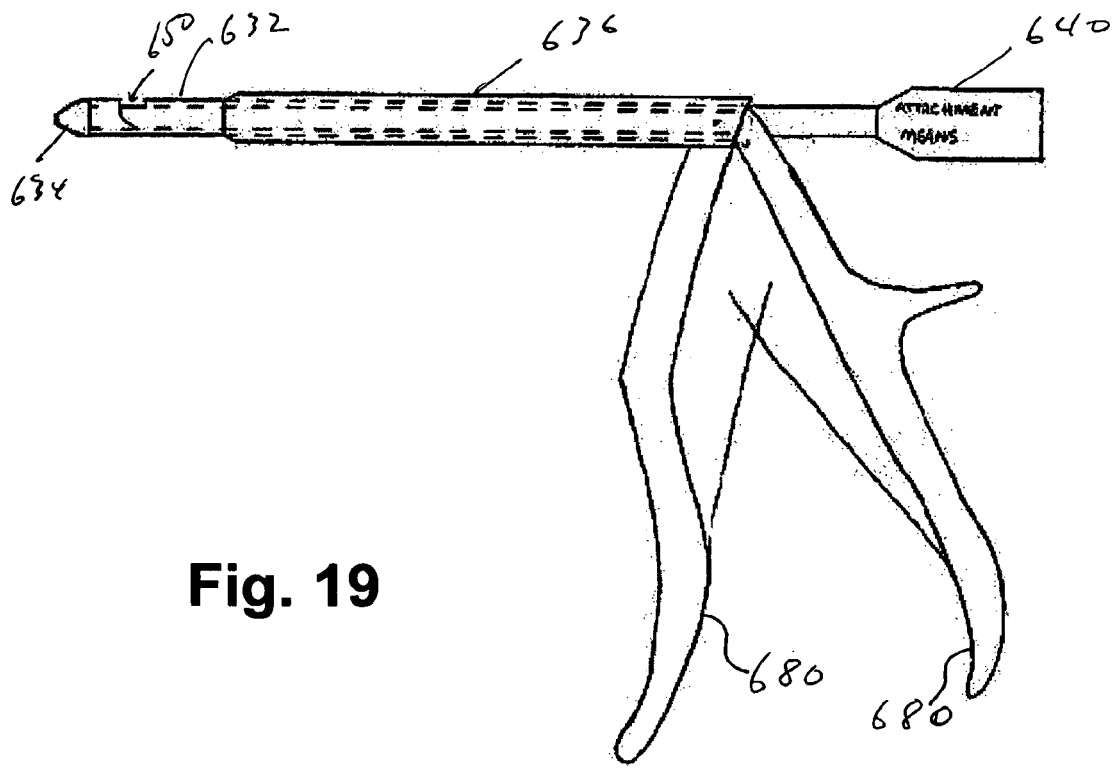
FIG. 19 is a schematic illustration of an apparatus for manipulating the cutting sleeve of FIG. 16 with the insertion cannula of FIG. 14.
Figure 20:
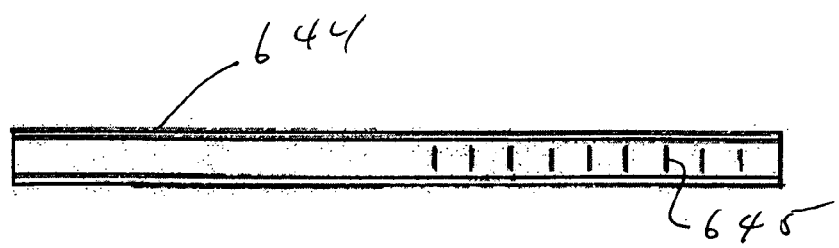
FIG. 20 is a schematic illustration of the tubular package for an elongated hydrogel prosthesis as used with the alternate embodiment of FIG. 13.
Figure 21:
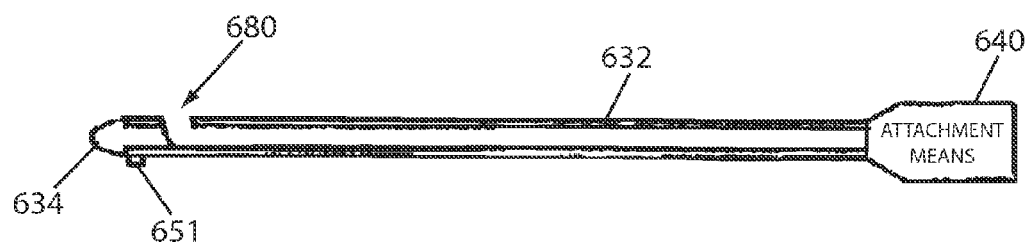
FIG. 21 is a schematic illustration of an embodiment of the apparatus illustrated in FIG. 13, incorporating an internal pressure transducer near the distal end of the insertion cannula.
Figure 22:
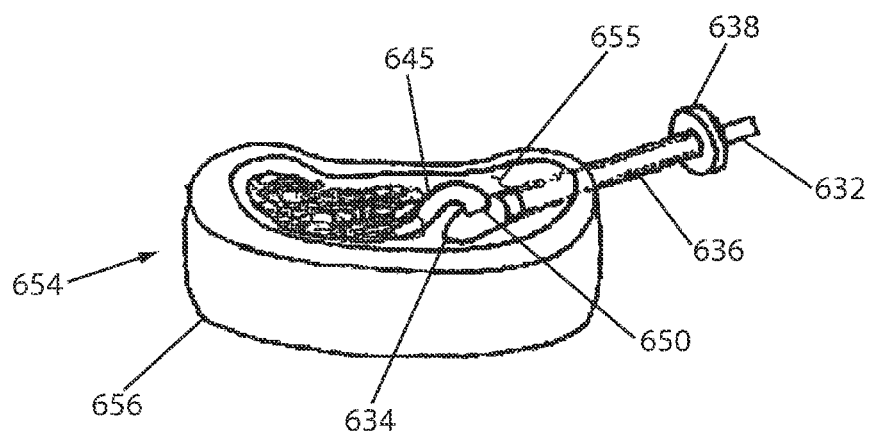
FIG. 22 is a schematic perspective view illustrating injection of an elongated hydrogel prosthesis into the nucleus pulposus region of an intervertebral disc using the embodiment of the invention illustrated in FIG. 13.
Figure 23:
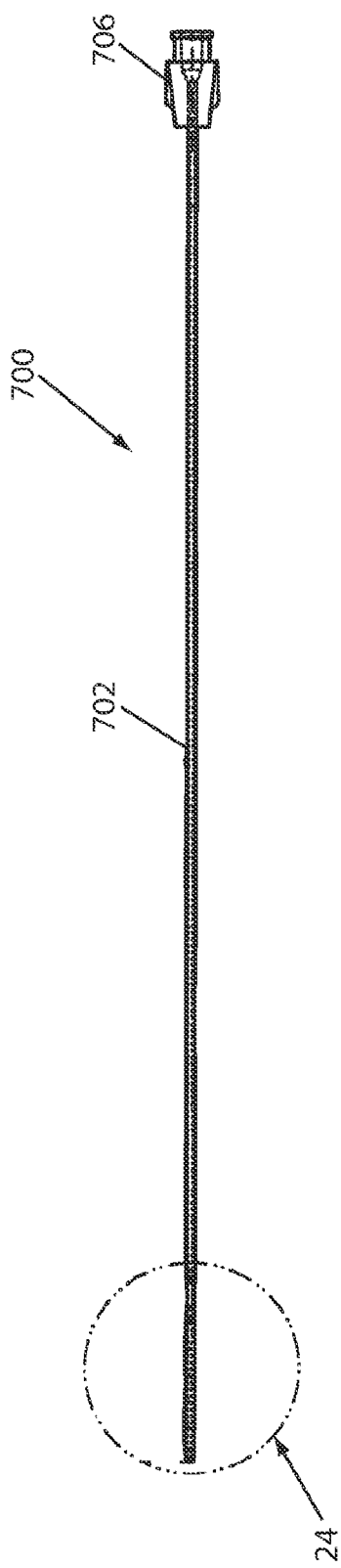
FIG. 23 is a side elevational view of a sizing balloon apparatus for measuring the volume of a defect or cavity within the nucleus pulposus region of an intervertebral disc.

In use, the embodiment 630 is used to insert an elongated hydrogel prosthesis into the nucleus pulpous region of an intervertebral disc either to supplement a degenerated nucleus pulposus or to fill a cavity created within the intervertebral disc by other surgical means, particularly minimally invasive surgical techniques. The injection apparatus 630 is assembled by coupling one end (a distal end) of a selected storage tube 644 containing an elongated hydrogel prosthesis 642 to the proximal end of delivery cannula 632 and coupling, in turn, a source of fluid pressure to the other (proximal) end of storage tube 644. The cutting sleeve 636 is then positioned over the delivery cannula 632. The pressure generator 648 is then operated to advance the hydrogel prosthesis 642 from the storage tube 644 through the delivery lumen 633 until the distal end of the prosthesis 642 just appears in the lateral delivery aperture 650. The cutting sleeve 636 is then advanced until it covers and protects the lateral delivery aperture 650, and the delivery cannula 632 is inserted into the surgical site and through an annulus fibrosus until the distal tip 634 and lateral delivery aperture 650 are located within the nucleus pulposus region of an intervertebral disc. This procedure is performed under control with radiological imaging or the like. The cutting sleeve is then retracted to expose the lateral delivery aperture 650, and the pressure generator 648 is operated to extrude the elongated hydrogel prosthesis 642 into the cavity within the intervertebral disc. When an appropriate amount of hydrogel has been implanted into the disc, as determined, e.g., by measuring the amount extruded from the storage tube 644 or by observing the implanted amount by radiology (using a radiopaque prosthesis), the cutting sleeve 636 is advanced over the lateral delivery aperture 650 to sever the elongated prosthesis 642. The delivery cannula 632 is then removed and surgical site closed by conventional procedures. An alternate embodiment of the insertion cannula 632 is illustrated in FIGS. 16 and 17, wherein an insertion cannula 662 is fitted with a tip 664 having a diameter somewhat larger than the diameter of the insertion cannula 662. The insertion cannula 662 has a lateral delivery aperture 670 and the tip 664 is provided with ramp 672, which may be either curved, as shown, or straight. In this embodiment the cutting sleeve 636 need not have a sharpened distal edge, as shown, e.g., in FIG. 18, but may have a somewhat blunter or square edge that can shear the hydrogel prosthesis extending from delivery aperture 670. FIG. 19 illustrates an apparatus having handles 680 that grip the delivery cannula 632 and the cutting sleeve 636 to permit the surgeon to advance the cutting sleeve 636 over the delivery cannula 632 in order to sever the hydrogel prosthesis extending form delivery aperture 650. FIG. 20 illustrates a prosthesis storage tube 644, having indicia 645 to indicate the length of the prosthesis 642 that has been extruded from the storage tube 644. Another alternate embodiment of the insertion cannula 632 is illustrated in FIG. 21. In the embodiment of FIG. 21, the insertion cannula 632 is provided with a pressure transducer 651 for determining the intradiscal pressure as the prosthesis is inserted. When this embodiment of the insertion cannula is used, the implantation can be terminated when a predetermined pressure within the intervertebral disc is reached. FIG. 22 schematically illustrates the insertion of an elongate hydrogel prosthesis 645 into the nucleus pulposus region 655 of an intervertebral disc 654 through the annulus fibrosus 656.

Figure 24:
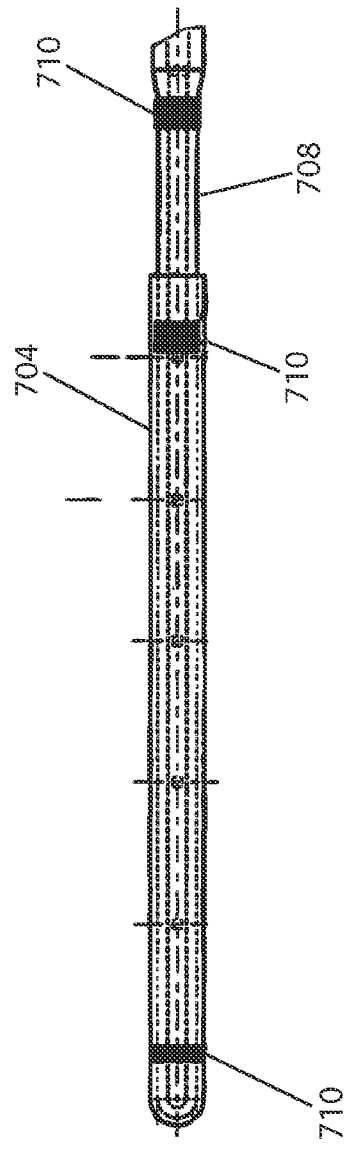
FIG. 24 is a detail of the tip of the sizing balloon apparatus of FIG. 23.
Figure 25:
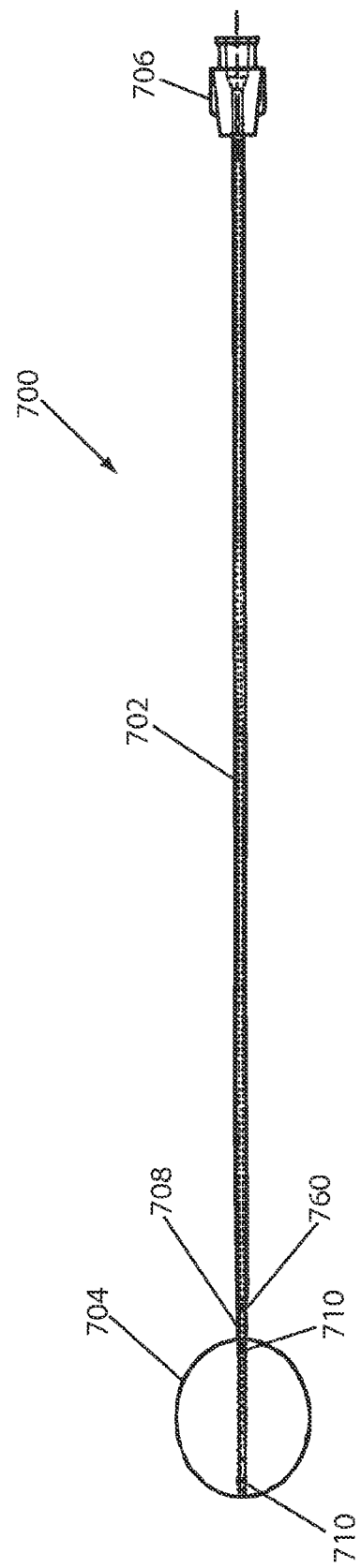
FIG. 25 is a side elevational view of the sizing balloon apparatus of FIG. 23 with sizing balloon in an expanded configuration.
Figure 26:
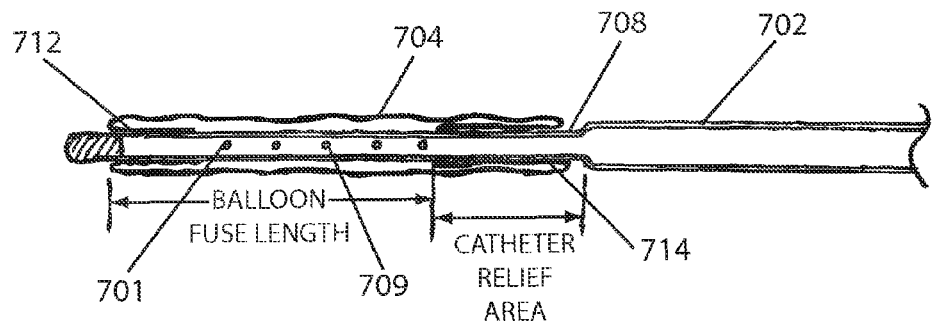
FIG. 26 is a schematic side elevational cross-sectional view of the distal region of the balloon sizing apparatus of FIG. 23, showing the sizing balloon in a collapsed or deflated configuration.
Figure 27:
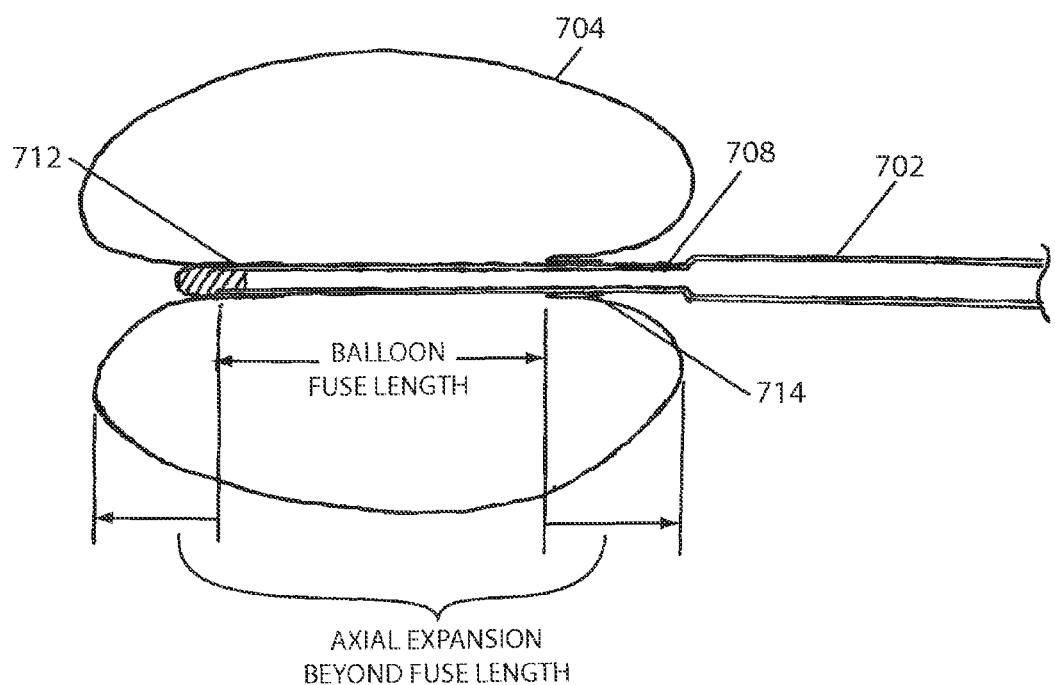
FIG. 27 is a schematic side elevational cross-sectional view of the distal region of the balloon sizing apparatus of FIG. 23, showing the sizing balloon in an expanded or inflated configuration.

A preferred apparatus 700 for determining the size of a cavity having a fillable volume within the nucleus pulposus region of an intervertebral disc in order to determine the volume of prosthesis to be injected is illustrated in FIGS. 23-27. Sizing apparatus 700 comprises an inflation catheter 702, having a diameter sized to fit through a prosthesis delivery cannula, e.g., the lumen 204 of delivery cannula 202, having a fluid coupling 706 at its proximal end, and having a highly compliant balloon 704 positioned on its distal end. In the illustrated embodiment, the balloon 704 surrounds the end of the catheter 702, which has a distal region 708 of reduced diameter to allow the balloon to collapse to a diameter not greater than the more proximal portion of the catheter 702. The entire catheter and balloon assembly is preferably sized to fit through the delivery lumen 204 of the delivery cannula 202 of the apparatus 100. The fluid coupling 706 at proximal end of the catheter is adapted to be attached to a source of fluid for inflating the balloon 704. Preferably the distal end of the catheter 702 extends through the balloon 704, and the balloon 704 is fastened to the reduced diameter region 708 of the catheter 702 at locations adjacent to the tip of the catheter 702 and a somewhat more proximal location within the reduced diameter region 708. Fluid for inflating the sizing balloon 704 enters and leaves the balloon through holes in the reduced diameter portion 708 of the catheter 702. Radiopaque markers 710 are positioned on the catheter 702, as shown in FIG. 24, in order to permit accurate location of the sizing balloon 704 with in the intervertebral disc by radioscopic control. The sizing balloon 704, as positioned on the catheter 702 prior to insertion, is in a collapsed state as shown in FIG. 26. FIG. 27 shows the sizing balloon 704 in its fully distended or fully expanded state, wherein sufficient inflating fluid, liquid or gas, has been introduced to expand the balloon 704 to a state wherein all folds, etc., of the collapsed state have been removed and further expansion of the balloon 704 requires elastic stretching of the bounding surface or membrane of the balloon 704. Although it is possible to further expand the balloon-beyond its fully distended state, it is preferred, according to the invention, to select a size of balloon 704 such that, when expanded with in a cavity, or the like, within an intervertebral disc, the balloon 704 never reaches its fully expanded state at the pressures employed to determine the size of the cavity, etc., within the intervertebral disc. Thus, in one embodiment of the sizing procedure of the invention, the balloon is inflated to a predetermined pressure that indicates that the intradiscal cavity is substantially filled. Such a predetermined pressure may range from about 5 to about 50 pounds per square inch (psi), preferably from about 15 psi to about 45 psi, or from about 25 psi to about 40 psi, or from about 30 psi to about 40 psi. A useful pressure for estimating a suitable volume of prosthesis to be injected is about 35 psi. Alternatively, or concurrently, the balloon can be inflated with a radiopaque fluid and the filling of the balloon can be radiographically monitored to determine the completion of filling of the cavity. The balloon must be highly compliant, i.e., it must undergo a relatively large change in volume per unit change in pressure. Accordingly, it is made of a very thin film of a strong, flexible synthetic resin. A preferred such material is a polyurethane, and a preferred balloon is made from a thin film of a polyurethane. In order to achieve maximum compliance of the sizing balloon 704 a balloon is selected and fitted to the sizing apparatus 700 that has an internal volume such that, as disclosed above, it will not reach its fully distended state when it is expanded within the intervertebral disc to a pressure that indicates a suitable volume of prosthesis for restoring, to the extent possible that natural mechanical properties of the intervertebral disc. Typically, a balloon having sufficient compliance to fit through a small delivery catheter and expand conformally to an intradiscal cavity, or the like, should be such that, when positioned at the distal end of an appropriate balloon inflation catheter and expanded between generally planar parallel plates spaced about 12 millimeters apart, it will reach its fully distended state when inflated with about 3 psi internal pressure. A balloon of such compliance is expected to expand within an intervertebral disc to fill any cavity, or the like, therein to a degree that accurately indicates a therapeutic volume of prosthesis to be inserted.

The invention having been described above in terms of certain embodiments, it will be apparent to those skilled in the art that many changes and alterations can be made without departing from the spirit or essential characteristics of the invention. All embodiments incorporating such changes are intended to be included within the invention. The present disclosure is therefore to be considered as illustrative and not restrictive, the scope of the invention being indicated by the appended claims, and all changes which come within the meaning and range of equivalency are intended to be included therein.

We claim:

1. A method for implanting a hydrogel prosthesis within an intervertebral disc, the method comprising the steps of:
   a) advancing a first guidewire through tissue surrounding an intervertebral disk until an end portion of said first guidewire contacts an outer wall of an annulus fibrosus of said intervertebral disc;
   b) advancing over said first guidewire a prosthesis insertion cannula, said prosthesis insertion cannula having a distal end adapted to be inserted through said annulus fibrosus of said intervertebral disc, a proximal end, and a delivery lumen extending between said proximal end and said distal end, said delivery lumen sized to slide over said first guidewire, said prosthesis insertion cannula being advanced until said distal end thereof contacts said outer wall of said annulus fibrosus;
   c) removing said first guidewire from said delivery lumen;
   d) advancing through said delivery lumen a second guidewire sized to be passed through said delivery lumen of said prosthesis insertion cannula and having a distal end adapted to pierce the annulus fibrosus of the intervertebral disc, until said distal end of the second guidewire has pierced said annulus fibrosus and extends into a nucleus pulposus region of said intervertebral disc;
   e) advancing said prosthesis insertion cannula over said second guidewire until said distal end of said prosthesis insertion cannula extends into said nucleus pulpous region of said intervertebral disc;
   f) removing said second guidewire from said delivery lumen, thereby leaving an open channel into said nucleus pulposus region of said intervertebral disc;
   g) optionally, removing nucleus pulposus tissue from said nucleus pulposus through said open channel;
   h) determining a volume within said intervertebral disc to be filled by said hydrogel prosthesis by inserting an inflatable highly compliant balloon through said delivery lumen of said prosthesis insertion cannula, inflating said balloon with a fluid such that the highly compliant balloon reaches a fully distended state when inflated with about 3 psi, the balloon being inflated to a pressure between 20 psi to 40 psi at which the intervertebral disc is adequately pressurized to restore the natural mechanical properties of the intervertebral disc and measuring the volume of said fluid required to inflate said balloon to said pressure of between 20 psi to 40 psi;
   i) coupling to said proximal end of said prosthesis delivery cannula a distal end of a storage tube, said storage tube containing a predetermined amount of the hydrogel prosthesis, said predetermined amount of hydrogel prosthesis substantially corresponding to said measured volume of said fluid;
   j) coupling a proximal end of said storage tube to a source of fluid pressure;
   k) applying said fluid pressure to said proximal end of said storage tube to force said hydrogel prosthesis through said delivery lumen of said prosthesis delivery cannula and into said nucleus pulposus region;
   l) removing said prosthesis delivery cannula from said intervertebral disc.

2. A method for implanting a hydrogel prosthesis within an intervertebral disc, the method comprising the steps of:
   inserting a highly compliant balloon in a collapsed state into said intervertebral disc;
   expanding said balloon within said intervertebral disc by introducing into said balloon a quantity of a pressurized fluid such that the highly compliant balloon reaches a fully distended state when expanded with about 3 psi, the balloon being expanded until an internal pressure within said balloon reaches a pressure between 20 psi to 40 psi at which the intervertebral disc is adequately pressurized to restore the natural mechanical properties of the intervertebral disc;
   measuring a volume of fluid required to inflate said balloon to said pressure of between 20 psi to 40 psi;
   deflating and removing the balloon from the intervertebral disc; and
   inserting a volume of hydrogel prosthesis that is at least substantially equal to the inflated volume of the balloon into the intervertebral disc.

3. The method of claim 2, wherein said pressure is in a range of from 30 psi to 40 psi.

4. The method of claim 2, wherein said pressure is 35 psi.

5. The method of claim 2, wherein said balloon is sized such that when expanded, said balloon never attains a fully distended state.

6. A method for injecting a hydrogel prosthesis into an intervertebral disc comprising the steps of:
   a) forming an access incision in a patient's skin;
   b) inserting a cannula through the incision into the intervertebral disc;
   c) determining a size of the intervertebral disc for receiving the hydrogel prosthesis, wherein the steps of determining the size of the intervertebral disc includes:
      i) inserting a sizing balloon through the cannula and into the intervertebral disc;
      ii) inflating the sizing balloon to a pressure of about 3 psi at which the balloon reaches a fully distended state;
      iii) continuing to inflate the sizing balloon to a pressure between 20 psi to 40 psi at which the intervertebral disc is adequately pressurized to restore the natural mechanical properties of the intervertebral disc;
      iv) determining an inflated volume of the sizing balloon required to achieve the pressure of between 20 psi to 40 psi;
      iv) selecting a tube containing a volume of hydrogel prosthesis, the volume of hydrogel prosthesis being at least substantially equal to the inflated volume of the sizing balloon;
      v) deflating the balloon; and
      vi) withdrawing the balloon from the intervertebral disc;
   d) inserting through the cannula the volume of hydrogel prosthesis that is at least substantially equal to the inflated volume of the sizing balloon;
   e) removing the cannula from the intervertebral disc; and
   f) closing the incision.

7. The method of claim 6, wherein step b) comprises:
   i) advancing a blunt guidewire having a distal end through the incision and towards the intervertebral disc until the distal end of the guidewire reaches an outer wall of the intervertebral disc;
   ii) advancing the cannula having a distal end over the guidewire until the distal end of the cannula reaches the outer wall of the intervertebral disc;
   iii) removing the blunt guidewire;
   iv) advancing a sharp guidewire through the cannula and through the outer wall of the intervertebral disc;
   v) advancing the cannula over the sharp guidewire until the distal end of the cannula lies within the intervertebral disc; and
   vi) removing the sharp guidewire.

8. The method of claim 6, where step c) iv) comprises:
   i) selecting a tube containing a predetermined amount of hydrogel prosthesis, the tube containing a volume of hydrogel prosthesis greater than the determined volume of the inflated sizing balloon;

ii) coupling the tube to an injection instrument; and iii) operating the injection instrument to extrude excess hydrogel prosthesis from the tube so that only the determined volume of hydrogel prosthesis to be injected into the intervertebral disc remains within the tube.

9. The method of claim 6, wherein step d) comprises:

i) coupling the tube to an injection instrument;

ii) operating the injection instrument to inject the hydrogel prosthesis into the intervertebral disc; and iii) inserting an end of a blunt instrument into the cannula to force any remaining hydrogel prosthesis from the cannula into the intervertebral disc.

10. The method of claim 6, wherein step c) ii) comprises inflating the sizing balloon to the pressure of 30 psi to 40 psi.

11. The method of claim 10, wherein step c) ii) comprises inflating the sizing balloon to the pressure of 35 psi.

12. The method of claim 6, wherein prior to step d), comprising the steps of:

i) coupling a pressure transducer to the cannula for determining an intradiscal pressure of the intervertebral disc as the prosthesis is injected;

ii) monitoring the intradiscal pressure of the intervertebral disc as the prosthesis is injected; and iii) terminating injection of the prosthesis if the pressure is reached.

13. The method of claim 6, wherein step c) i) further comprises visualizing a location of the sizing balloon as the sizing balloon is being inserted into the intervertebral disc via a plurality of radiopaque markers.

14. The method of claim 6, wherein the sizing balloon is inflated to a size below its fully distended state.

15. The method of claim 6, wherein the sizing balloon is highly compliant.

16. The method of claim 6, wherein the volume of hydrogel prosthesis in step c) iv) is equal to the volume of the sizing balloon.

17. The method of claim 6, comprising the further step of:

g) urging an excess volume of the volume of hydrogel prosthesis of step c) iv) out of the cannula after step e), wherein the volume of hydrogel prosthesis in step c) iv) is greater than the volume of the sizing balloon.

18. A method for implanting an injectable prosthesis within an intervertebral disc, the method comprising the steps of:

a) gaining access to the intervertebral disc;

b) inserting a highly compliant balloon in a collapsed state into the intervertebral disc;

c) expanding the balloon by introducing a quantity of a pressurized fluid into the balloon such that the highly compliant balloon reaches a fully distended state when inflated with about 3 psi, the balloon being expanded until pressure in the balloon reaches a pressure between 20 psi to 40 psi at which the intervertebral disc is adequately pressurized to restore the natural mechanical properties of the intervertebral disc;

d) measuring the volume of fluid required to inflate the balloon to the pressure of between 20 psi to 40 psi;

e) deflating and removing the balloon from the intervertebral disc;

f) injecting the measured volume of fluid of the injectable prosthesis into the intervertebral disc.

* * * * *